(12) United States Patent
Wu et al.

(10) Patent No.: US 8,969,406 B2
(45) Date of Patent: *Mar. 3, 2015

(54) USE OF COMPOUND FOR INHIBITING GLUTATHIONE S-TRANSFERASE OMEGA 1 ACTIVITY AND METHOD FOR SYNTHESIZING THE SAME

(71) Applicant: China Medical University, Taichung (TW)

(72) Inventors: Yang-Chang Wu, Kaohsiung (TW); Kuo-Hsiung Lee, Kaohsiung (TW); Fang-Rong Chang, Kaohsiung (TW); Da-Wei Chuang, Hsinchu County (TW); Juan-Cheng Yang, Tainan (TW)

(73) Assignee: China Medical University, Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/845,119

(22) Filed: Mar. 18, 2013

(65) Prior Publication Data

US 2014/0221470 A1 Aug. 7, 2014

(30) Foreign Application Priority Data

Feb. 7, 2013 (TW) .............................. 102104891 U

(51) Int. Cl.
C07D 311/92 (2006.01)
A61K 31/352 (2006.01)
A61P 35/00 (2006.01)
C07D 311/00 (2006.01)

(52) U.S. Cl.
CPC ............ *C07D 311/92* (2013.01); *A61K 31/352* (2013.01); *C07D 311/00* (2013.01)
USPC ............ 514/455; 514/454; 549/389; 549/392

(58) Field of Classification Search
CPC ........................... C07D 311/92; A61K 31/352
USPC ..................... 514/454, 455; 549/389, 392
See application file for complete search history.

(56) References Cited

U.S. PATENT DOCUMENTS

| 7,550,160 B2 | 6/2009 | Wu et al. |
| 7,670,630 B2 | 3/2010 | Wu et al. |
| 7,785,639 B2 | 8/2010 | Wu et al. |
| 7,842,721 B2 | 11/2010 | Lin et al. |

FOREIGN PATENT DOCUMENTS

TW 200840561 A 10/2008

OTHER PUBLICATIONS

Chen et al., A novel synthetic protoapigenone analogue, WYC02-9, induces DNA damage and apoptosis in DU145 prostate cancer cells through generation of reactive oxygen species, Free Radical Biology &Medicine, 2011, pp. 1151-1162.
Attila Hunyadi et al., Direct Semi-Synthesis of the Anticancer Lead-Drug Protoapigenone from Apigenin and Synthesis of Further New Cytotoxic Protoflavone Derivatives, PLoS ONE, Aug. 2011, vol. 6, Issue 8: e23922.
Chiu et al., Fern Plant—Derived Protoapigenone Leads to DNA Damage, Apoptosis, and G2/M Arrest in Lung Cancer Cell Line H1299, DNA and Cell Biology, col. 28, Nov. 10, 2009, pp. 501-506.
Lin et al., First Total Synthesis of Protoapigenone and Its Analogues as Potent Cytotoxic Agents, J. Med. Chem. Jul. 10, 2007, pp. 3921-3927.

(Continued)

*Primary Examiner* — Sreeni Padmanabhan
*Assistant Examiner* — Irina Neagu
(74) *Attorney, Agent, or Firm* — CKC & Partners Co., Ltd.

(57) ABSTRACT

A compound for inhibiting activity of glutathione s-transferase omega 1 is provided and is represented by the following Formula 1:

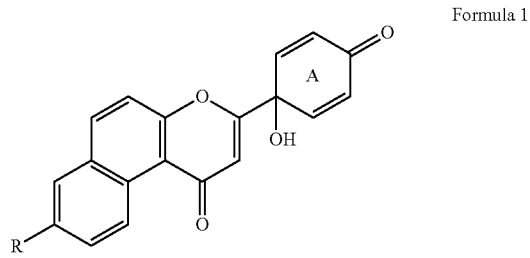

Formula 1 in which A is p-quino, and R is selected from the group consisting of the following Formula 1a and Formula 1b, where n in Formula 1 is 1 or 2, m in Formula 1b is 1 or 2, and n' in Formula 1b is 1, 2, or 3:

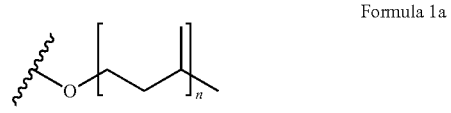

Formula 1a

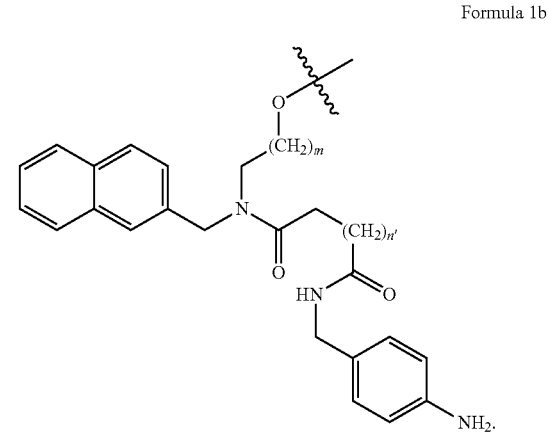

Formula 1b

1 Claim, 2 Drawing Sheets

(56) References Cited

OTHER PUBLICATIONS

Danko et al., In Vitro Cytotoxic Activity of Novel Protoflavone Analogs—Selectivity Towards a Multidrug Resistant Cancer Cell Line, Anticaner Research, 2012, pp. 2863-2870.

Wang et al., Inhibition of ATR-Dependent Signaling by Protoapigenone and Its Derivative Sensitizes Cancer Cells to Interstrand Cross-link—Generating Agents In Vitro and In Vivo, American Association for Caner Research, Apr. 24, 2012, pp. 1443-1453.

Tung et al., Inhibition of the Epstein-Barr virus Iytic cycle by protoapigenone, Journal of General Virology, 2011, pp. 1760-1768.

Chang et al., Protoapigenone, a Novel Flavonoid, Induces Apoptosis in Human Prostate Cancer Cells through Activation of p38 Mitogen-Activated Protein Kinase and c-Jun NH2-Terminal Kinase 1/2, Pharmacology and Experimental Therapeutics, JPET vol. 325, pp. 841-849, 2008.

Chen et al., Protoapigenone, a natural derivative of apigenin, induces mitogen-activated protein kinase-dependent apoptosis in human breast cancer cells associated with induction of oxidative stress and inhibition of glutathione S-transferase, Invest New Drugs, vol. 29, pp. 1347-1359, 2011.

Chang et al., Protoapigenone, a novel flavonoid, inhibits ovarian cancer growth in vityo and in vivo, Cancer Letters, 2008, pp. 85-95.

Chuang et al., Synthesis of Flavones and γ-Benzopyranones Using Mild Sonogashira Coupling and 18-Crown-6 Ether Mediated 6-endo Cyclization, European Journal of Organic Chemistry, Issue 24, pp. 4533-4540, Aug. 2012.

Chen et al., Total Synthetic Protoapigenone WYC02 Inhibits Cervical CancerCell Proliferation and Tumour Growth through PIK3 Signalling Pathway, Basic & Clinical Pharmacology & Toxicology, 2013, pp. 8-18.

USE OF COMPOUND FOR INHIBITING GLUTATHIONE S-TRANSFERASE OMEGA 1 ACTIVITY AND METHOD FOR SYNTHESIZING THE SAME

RELATED APPLICATIONS

The application claims priority to Taiwan Application Serial Number 102104891, filed Feb. 7, 2013, which is herein incorporated by reference.

BACKGROUND

1. Field of Invention

The present disclosure relates to a compound for inhibiting glutathione s-transferase omega 1 activity, a pharmaceutical composition containing thereof, and a method for synthesizing the same.

2. Description of Related Art

Nowadays, Multi-Drug Resistance (MDR) is believed to be one of the essential topics of pharmaceutical drug research and development on cancer therapy. In addition to the well known channel proteins like p-glycoprotein, MRP1, ABCG2, etc, protein enzymes as metabolic drugs have also been gradually given attention in the field of pharmaceutical drug development. In which, Glutathione S-Transferase (GST) family protein have been playing a critical role.

The GSTs is a phase II metabolic enzyme that favors detoxification of foreign substances of cells; the foreign substances will be linked with glutathione by the GSTs in order to reduce their toxicities. Thus, GST family proteins have been found to be highly expressed in various cancer cells. However, both the fundamental and clinical researches indicated that the GSTs have been an important factor involved in drug resistance.

It was found in many studies that one of a protein of the GSTs, GST pi, was essential in association with the acquired resistance to certain anticancer drugs, and thus the GST pi inhibitors have been put under the spotlight by pharmaceutical drug researchers and developers as a main discovering target so as to eliminate such a drug resistance effect. For instance, Telik Biopharmaceutical Company received a great amount of patents of various GST pi inhibitors, some of which have been made as drugs, such as TELCYTA® (Canfosfamide HCl) and TELINTRA® (Ezatiostat HCl, TLK199).

Other isoforms of GSTs, namely GST omega family, such as GST omega 1-1 have been found to be closely associated with drug resistance effects against adriamycin, etoposide, and platinum anticancer drugs. Furthermore, a depletion of GST omega 1-1 in cancer cells circumvents drug resistances against arsenic trioxide, cisplatin, daunorubicin, and etoposide.

Nevertheless, inhibitors of GST omega 1 are yet to be discovered nor developed for addressing the drug resistance effects in cancer cells.

SUMMARY

According to a first embodiment of the present disclosure, a compound for inhibiting glutathione s-transferase omega 1 activity is represented by the following Formula 1:

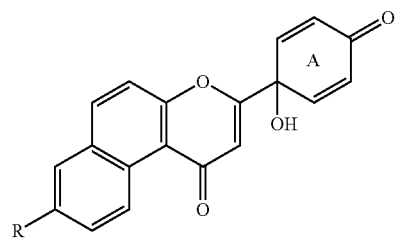

[Formula 1]

In which A is p-quino, and R is selected from the group consisting of the following Formula 1a and Formula 1b, where n in Formula 1 is 1 or 2, m in Formula 1b is 1 or 2, and n' in Formula 1b is 1, 2, or 3:

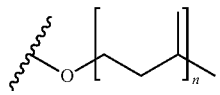

[Formula 1a]

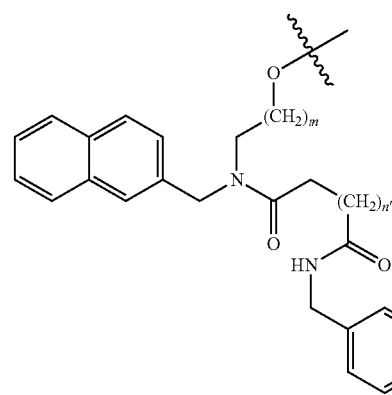

[Formula 1b]

According to a second embodiment of the present disclosure, a medical composition for inhibiting activity of glutathione s-transferase omega 1 comprises an effective amount of a compound of the aforementioned Formula 1 and a pharmaceutically acceptable carrier.

According to a third embodiment of the present disclosure, a method for synthesizing a compound of Formula 1 according to claim 1, comprises the following steps: performing a Friedel-Crafts acylation reaction on 2,6-Dimethoxynaphthalene, adding a halogen reagent for removing two methoxy groups, adding a first protecting group and performing a condensation reaction between the first group and a p-hydroxybenzaldehyde having a second protecting group, adding a halogen catalyst; adding an acidic solution for removing the first protecting group, adding an unsaturated carbon chain having halogen, removing the second protecting group and performing an oxidation reaction by adding a hypervalent iodine compound for obtaining the compound represented by the aforementioned Formula 1.

According to an example of the third embodiment, in which the halogen reagent can be Boron tribromide.

According to another example of the third embodiment, the first protecting group can be Methoxymethyl (MOM).

According to another example of the third embodiment, in which the second protecting group can be benzyl.

According to another example of the third embodiment, in which the halogen reagent can be iodine.

According to another example of the third embodiment, in which the acidic solution can be hydrochloric acid solution.

According to another example of the third embodiment, in which the unsaturated carbon chain can be geranyl bromide.

According to another example of the third embodiment, in which the hypervalent iodine compound can be bis-(tri-fluoroacetoxy)-iodobenzene.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
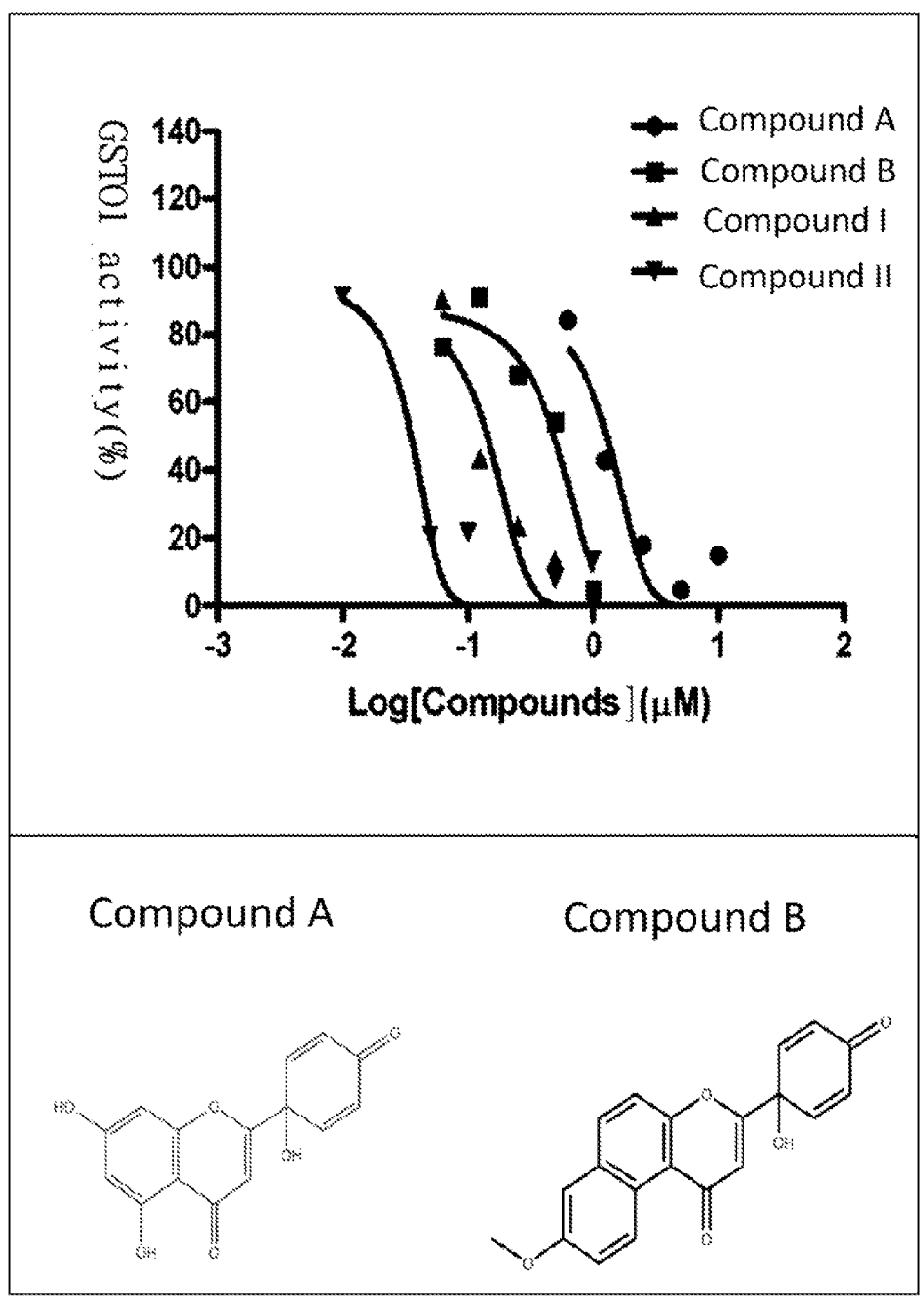
FIG. 1 is the result of GSTO1 enzyme activity effected by different compounds having different side chains.

In the following detailed description, for purposes of explanation, numerous specific details are set forth in order to provide a thorough understanding of the disclosed embodiments. It will be apparent, however, that one or more embodiments may be practiced without these specific details.

A compound for inhibiting activity of glutathione s-transferase omega 1 is provided and is represented by the following Formula 1:

[Formula 1]

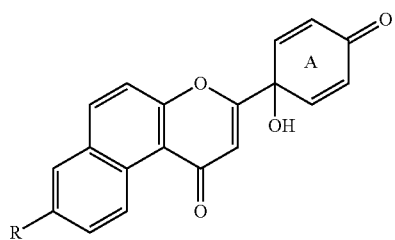

where A is p-quino, and R is selected from the group consisting of the following Formula 1a and Formula 1b, where n in Formula 1 is 1 or 2, m in Formula 1b is 1 or 2, and n' in Formula 1b is 1, 2, or 3:

[Formula 1a]

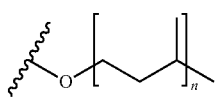

-continued

[Formula 1b]

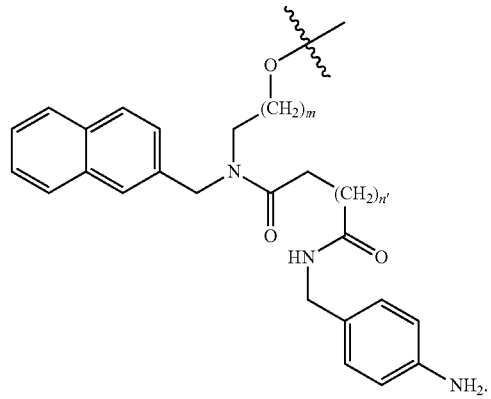

The compound is artificially designed and synthesized to be an inhibitory structure binding against the active site of glutathione s-transferase omega 1, which can be applied as a potential pharmaceutical drug for inhibiting cancer cell growth or even killing cancer cells in the future.

EXAMPLES

The following examples are described for those skilled in the art to further understand the present disclosure and should not be limited to the present disclosure.

1. Cancer Cell Growth Inhibitory Effect Analysis

For evaluating the in vitro growth inhibitory concentrations (GI150, μM) of the compound represented by Formula 1 of the present disclosure, human oralepithelial carcinoma cell line (KB), multidrug-resistant nasopharyngeal carcinoma cell line (KB-Vin), human lung adenocarcinoma cell line (A549), and prostate cancer cell line (DU145) were used in the following experiment. The GI50 values of Paclitaxel, an anticancer chemotherapy drug, were used as control. The result of this experiment are shown in Table 1.

As shown in Table 1, compounds with side chain No. 11 or No. 12 has better inhibitory effect against the four aforementioned experimental cancer cells when compared with the others having other kinds of side chains.

Further, the compound having side chain No. 11 is an isopentane monomer with an ether linkage, and the GI50 value of such a compound inhibiting against KB cell, KB-Vin cell, A549 cell, and DU145 cell is 0.2 μM, 0.269 μM, 0.382 μM, and 0.231 μM, respectively. Obviously, the GI50 value of the compound having side chain No. 11 is well and better than the others having other kinds of side chains except the one having side chain No. 12.

Additionally, the compound having side chain No. 12 has two isopentane monomers on its side chain. The GI50 value of such a compound against KB cell, KB-Vin cell, A549 cell, and DU145 cell is 0.067 μM, 0.335 μM, 0.233 μM, and 0.065 μM, respectively; this compound has a more significant inhibitory effect against KB cell and DU145 cell when compared to the compound having side chain No. 11.

It is worth to be mentioned that, while increasing the number of isopentane monomer on the side chains to three isopentane monomers, the inhibitory effect against the cancer cells will be significantly reduced (see Table 1; the compound having side chain No. 13). As a result, the inhibitory effect of cancer cells inhibited by the compound not only depends on the stereo structure of isopentane monomer, but the number of isopentane monomer also effects.

TABLE 1

| | Cancer cell growth inhibitory effect | | | | |
|---|---|---|---|---|---|
| No. of side chains | In vitro cytotoxicity assay: GI$_{50}$ (μM) | | | | |
| | | KB cell | KB-Vin cell | A549 cell | DU145 cell |
| Compound main structure | *[naphthopyranone with hydroxycyclohexadienone structure]* | 0.865 | 0.674 | 0.763 | 0.799 |
| 1 | *[methyl acetate]* | 0.718 | 0.66 | 0.895 | 0.688 |
| 2 | *[methyl propanoate]* | 0.694 | 0.668 | 0.811 | 0.694 |
| 3 | *[methyl butanoate]* | 0.669 | 0.664 | 0.731 | 0.695 |
| 4 | *[methyl pentanoate]* | 0.629 | 0.663 | 0.738 | 0.656 |
| 5 | *[methyl isovalerate]* | 0.644 | 0.651 | 0.656 | 0.795 |
| 6 | *[methyl morpholine carboxylate]* | 0.607 | 0.64 | 0.603 | 0.617 |
| 7 | *[methyl piperidine carboxylate]* | 0.615 | 0.619 | 0.536 | 0.522 |
| 8 | —OMe | 0.871 | 0.692 | 0.811 | 0.707 |
| 9 | *[methoxypropyl]* | 0.68 | 0.704 | 0.693 | 0.682 |
| 10 | *[dimethoxymethane ether]* | 0.786 | 0.766 | 0.819 | 0.865 |
| 11 | *[isopentyl methyl ether]* | 0.2 | 0.269 | 0.382 | 0.231 |
| 12 | *[branched alkyl ether]* | 0.067 | 0.335 | 0.233 | 0.065 |
| 13 | *[branched alkyl ether]* | 1.115 | 1.883 | 4.27 | 1.262 |

TABLE 1-continued

Cancer cell growth inhibitory effect

| No. of side chains | In vitro cytotoxicity assay: GI$_{50}$ (μM) | | | | |
|---|---|---|---|---|---|
| | | KB cell | KB-Vin cell | A549 cell | DU145 cell |
| 14 | [structure: methoxyethyl-N(CH3)2] | 0.683 | 0.841 | 0.754 | 0.808 |
| 15 | [structure: methoxyethyl-N(Et)2] | 0.644 | 1.325 | 0.551 | 0.685 |
| 16 | [structure: methoxyethyl-N(iPr)2] | 0.55 | 0.682 | 0.584 | 0.62 |
| 17 | [structure: methoxyethyl-piperidine] | 0.499 | 0.675 | 0.483 | 0.541 |
| 18 | [structure: methoxyethyl-pyrrolidine] | 0.552 | 1.108 | 0.628 | 0.693 |
| 19 | —OH | 0.944 | 0.738 | 0.806 | 0.709 |
| Control (Paclitaxel) | | 4.64 nm | >1000 nM | 3.56 nM | 3.00 nM |

2. Enzyme Activity Essay of GST Omega 1 (GSTO1)

The following experiment is to prove that the inhibition of the cancer cell growth caused by the compound having side chain No. 11 or No. 12 mentioned above is associated with the inhibitory effect of GSTO1 enzyme activity.

This experiment procedures refers to a GSTO1 substrate assay published by Bachovchin et al. in 2009, which uses (S-(4-nitrophenacyl)glutathione; 4NPG) as the specific GSTO1 substrate for evaluating the enzyme activity thereof. First, 100 μl mixture having 2 nM GSTO1, 100 mM Tris (pH 8.0), 1.5 mM EDTA, and 10 mM 2-mercaptoethanol were added into each well of an UV-penetrable 96-well culture plate. Besides, 100 μl buffer having 100 mM Tris (pH 8.0), 1.5 mM EDTA, and 10 mM 2-mercaptoethanol were used as blank control.

The compound (main structure is represented by Formula 1) to be tested in this assay, having an additional side chain No. 11 and an additional side chain No. 12, respectively, were represented as compound I and compound II. Furthermore, compound A and compound B were controls in this assay, in which compound A does not contain the main structure (Formula 1) of the present disclosure, whereas compound B contains the main structure (Formula 1) of the present disclosure and has a methyl side chain on the main structure (Formula 1). The structure of compound A and compound B are shown in FIG. 1, and the structure of compound I and compound II are shown in the following:

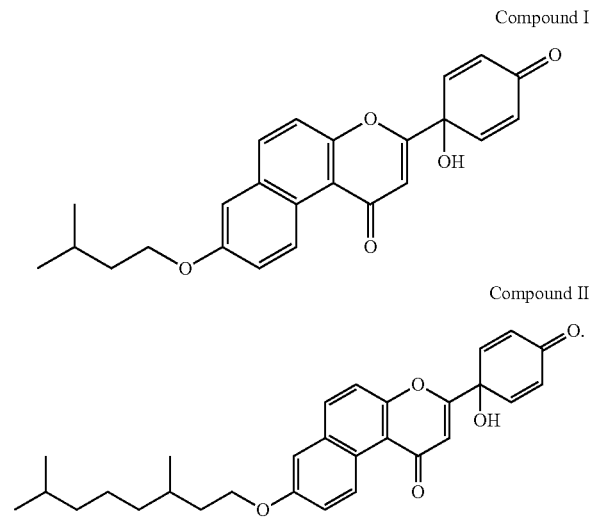

Compound I

Compound II

Compound I, compound II, compound A, and compound B were mixed and reacted with dimethyl sulfoxide, respectively, and were added into wells of a 96-well culture plate; the reaction time is 30 min, and the reaction temperature is 25° C. Then, 4NPG were added to each of the aforementioned mixture to a final concentration of 0.5 mM.

The substrate 4NPG can specifically bind to GSTO1, and the structure of the aforementioned compound I and compound II were designed to competitively and structurally bind to the substrate binding site (active site), so that the competitory effect between compound I and 4NPG, or compound II and 4NPG, can be estimated by measuring O.D.$_{305}$ absorbance of each of the mixtures mentioned above in every minute, after calibrating with the blank control.

FIG. 1 is the result of GSTO1 enzyme activity effected by different compounds having different side chains. Referring to the result, the inhibitory effect of compound A, which does not contain the main structure (Formula 1) of the present disclosure, and compound B, which contains the main structure (Formula 1) of the present disclosure having side chains without isopentane monomer, against GSTO1 is slight, whereas the compound I and compound II of the present disclosure remains significant results of competitively binding with GSTO1 against 4NPG. In addition, the inhibitory effect increases as the side chain extends; this results exactly matches the result of the aforementioned example 1 (see Table 1).

3. Compound Synthesis

As described above, the GSTO1 inhibitory effect of compound II (Formula 1 having side chain No. 12) of the present disclosure is greater than the others, and the structure of compound II has been proven that it is able to competitively bind to the GSTO1 active site against its substrate, 4NPG.

Figure 2:
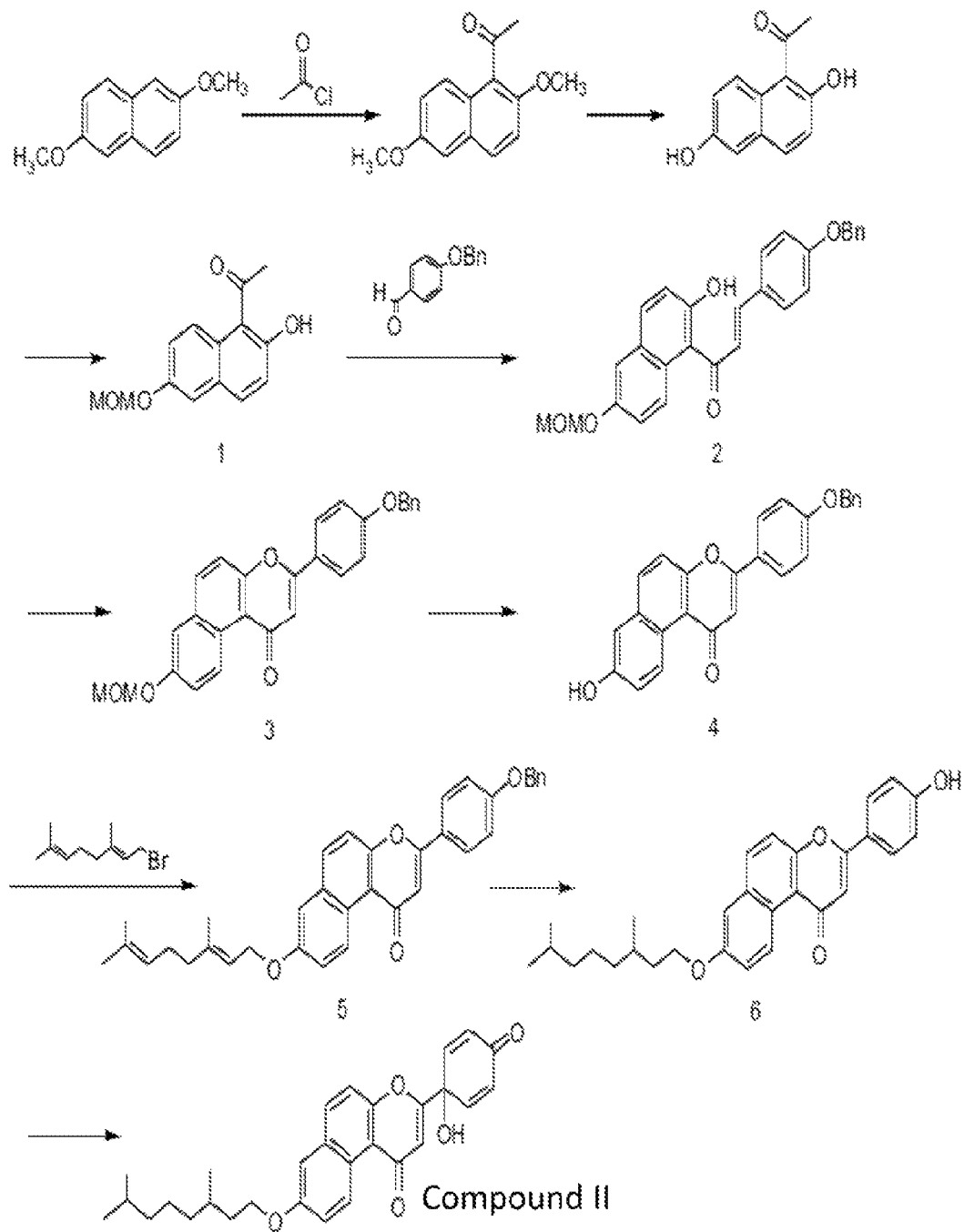
FIG. 2 is a flow chart illustrating a method for synthesizing a compound II of the present disclosure.

FIG. 2 is a flow chart illustrating a method for synthesizing the compound II of the present disclosure.

First, anhydrous benzene solution containing 2,6-dimethoxynaphthalene were added to 1.6 N stannic chloride and stirred in a nitrogen environment. Then, 1.5 N acetyl chloride were added dropwise and stirred overnight. Afterwards, benzene were removed by using a rotary evaporator, and then the mixture were extracted with dichloromethane/H$_2$O. Dichloromethane were eliminated by using a rotary evaporator, then, the extraction were separated by an n-hexane/ethyl acetate column. After separation, 1-acetyl-2,6-dimethoxynaphthalene can be obtained, and the yield is 86.5%.

Afterwards, 1-acetyl-2,6-dimethoxynaphthalene was dissolved in anhydrous dichloromethane, and 6 N tribromoborane were added in a nitrogen environment at −78° C. and stirred. After stirring for 2 hours, water was added for removing the remaining tribromoborane. The remaining organic solvents were eliminated by using a rotary evaporator, and then this mixture were separated by an n-hexane/ethyl acetate column. After separation, 1-acetyl-2,6-dihydroxy naphthalene can be obtained, and the yield is 93%.

1-acetyl-2,6-dihydroxy naphthalene was dissolved in anhydrous dichloromethane, and 2 N of N,N-diisopropylethylamine were added to the mixture on ice continuously until the mixture became transparent. Chloroethyl methyl ether was diluted 40 times with dichloromethane and then added to the mixture dropwise and stirred. After stirring for 2 hours, the remaining organic solvents in the mixture were removed by using a rotary evaporator, and then this mixture were separated by an n-hexane/ethyl acetate column. After separation, compound 1 can be obtained, and the yield is 47.3%.

Claisen-Schmidt condensation was performed between compound 1 and 4-benzyloxy-benzaldehyde. 3 N 4-benzyloxybenzaldehyde were added into an ethanol solution containing compound 1 and stirred, and then 50% potassium hydroxide solution were added to the ethanol solution with a volume mixing ratio of 1:1. After stirring in 55° C. for 1.5 hours, organic solvents were removed by using a rotary evaporator, and then this mixed solution were separated by an n-hexane/ethyl acetate column. After separation, chalcone compound 2 can be obtained, and the yield is 92.6%.

Compound 2 was dissolved in a proper amount of pyridine with 2 N iodine added. After heat refluxing overnight, sodium thiosulfate was added and then the whole mixture was extracted with ethyl acetate/water, the organic layer of the extract was removed and then the extract was separated by column chromatography for obtaining (3-naphthalene flavone compound 3; the yield is 65%.

Compound 3 was then dissolved in a proper amount of a dichloromethane solution added with a hydrochloric acid/isopropanol solution with a mixing ratio of 1:10. After stirring overnight, and filtering the precipitate of the mixture, compound 4 was obtained. Anhydrous dimethyl amide solution containing 2 N sodium hydride was dropwise added to a dimethyl amide solution containing compound 4 on ice and in a nitrogen environment until the color of the mixture turns into red. Afterwards, 2N geranyl bromide solution were added into the mixture. Water was added after the mixture was stirred in room temperature for 2 hours, and then the mixture was extracted with ethyl acetate. The remaining organic solvents were removed by using a rotary evaporator, and then this mixture were separated by a dichloromethane/methanol column. After separation, compound 5 can be obtained, and the yield is 94%.

Compound 5 was dissolved in ethyl acetate, and then 10% palladium carbon were added. After catalyzing with hydrogen gas overnight, filtering palladium carbon, and removing organic solvents by a rotary evaporator, compound 6 with benzyl removed was obtained, and the yield is 40%.

Finally, compound 6 was dissolved in a Acetonitrile/water=15:1 solution, and then added with 2 N [bis(trifluoroacetoxy)iodo]benzene for oxidation, compound II having two isopentane monomers on its side chain was obtained, and the yield is 49%.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the invention. In view of the foregoing, it is intended that the present disclosure cover modifications and variations of this invention provided they fall within the scope of the following claims.

What is claimed is:

1. A method for inhibiting glutathione s-transferase omega 1 activity, comprising administering an effective amount of a compound of the following Formula 1:

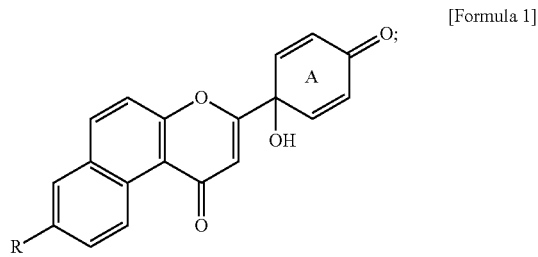

[Formula 1]

wherein A is p-quino, and R is the following Formula 1a, where n in Formula 1a is 1 or 2:

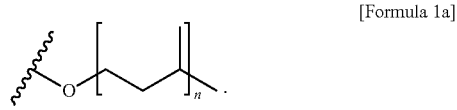

[Formula 1a]

* * * * *